United States Patent [19]

Smith et al.

[11] 3,954,779

[45] May 4, 1976

[54] 4-(4'-HYDROXYCYCLOHEXYL)-2,2,6,6-TETRAMETHYL PIPERIDINES

[75] Inventors: Malcolm John Smith; Donald Richard Randell, both of Stockport, England

[73] Assignee: Ciba-Geigy Corporation, Ardsley, N.Y.

[22] Filed: Apr. 1, 1974

[21] Appl. No.: 456,919

[30] Foreign Application Priority Data

Apr. 5, 1973 United Kingdom............... 16248/73

[52] U.S. Cl....................... 260/293.65; 260/45.8 N; 260/293.62; 260/293.72; 260/293.74; 260/293.75; 260/293.81; 260/293.82; 260/293.83; 260/293.84; 260/294.9; 260/295 R; 260/297 R
[51] Int. Cl.²...................................... C07D 211/22
[58] Field of Search.................. 260/293.65, 293.74, 260/293.81, 293.83, 293.84, 293.62, 293.72, 293.75, 293.82

[56] References Cited
UNITED STATES PATENTS

| | | | |
|---|---|---|---|
| 3,513,170 | 5/1970 | Murayama et al............. | 260/293.65 |
| 3,828,052 | 8/1974 | Holt et al...................... | 260/293.65 |

*Primary Examiner*—Sherman D. Winters
*Attorney, Agent, or Firm*—Nestor W. Shust

[57] ABSTRACT

A compound having the formula:-

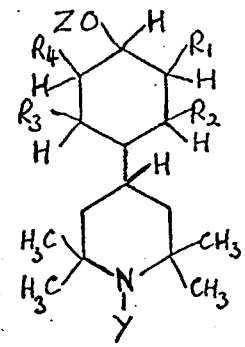

I and salts thereof, wherein $R_1$, $R_2$, $R_3$ and $R_4$ are the same or different and each is hydrogen, an alkyl residue having from 1 to 9 carbon atoms, a cycloalkyl residue having from 5 to 14 carbon atoms or a cycloalkyl-alkyl residue having from 7 to 14 carbon atoms, Y is hydrogen, 0°, an alkyl residue having from 1 to 4 carbon atoms, or an aralkyl residue having from 7 to 12 carbon atoms and Z is hydrogen, an unsubstituted or substituted alkyl residue having from 1 to 20 carbon atoms, an alkenyl or alkynyl residue having from 2 to 20 carbon atoms, a cycloalkyl residue having from 5 to 12 carbon atoms, an aralkyl residue having from 7 to 12 carbon atoms, an aryl residue having from 6 to 12 carbon atoms, or the group having the formula: wherein $Z_1$ has the same significance as Z as hereinbefore defined, or $Z_1$ is a group $-NR_5R_6$ wherein $R_5$ is hydrogen or an alkyl residue having from 1 to 4 carbon atoms and $R_6$ is hydrogen, an alkyl group having from 1 to 20 carbon atoms, a cycloalkyl group having from 5 to 12 carbon atoms, an aralkyl residue having from 7 to 12 carbon atoms or an aryl residue having from 6 to 12 carbon atoms having light stabilising activity.

10 Claims, No Drawings

4-(4'-HYDROXYCYCLOHEXYL)-2,2,6,6-TETRAMETHYL PIPERIDINES

The present invention relates to new chemical compounds and in particular to new 4-(4'-hydroxycyclohexyl)2,2,6,6-tetramethyl piperidines and derivatives thereof, processes for their production and compositions containing these compounds.

According to the present invention, there is provided a compound having the formula:

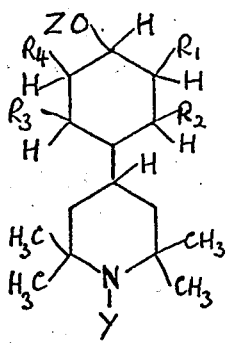

and salts thereof, wherein $R_1$, $R_2$, $R_3$ and $R_4$ are the same or different and each is hydrogen, an alkyl residue having from 1 to 9 carbon atoms, a cycloalkyl residue having from 5 to 14 carbon atoms or a cycloalkyl-alkyl residue having from 7 to 14 carbon atoms, Y is hydrogen, 0, an alkyl residue having from 1 to 4 carbon atoms, or an aralkyl residue having from 7 to 12 carbon atoms and Z is hydrogen, an unsubstituted or substituted alkyl residue having from 1 to 20 carbon atoms, an alkenyl or alkynyl residue having from 2 to 20 carbon atoms, a cycloalkyl residue having from 5 to 12 carbon atoms, an aralkyl residue having from 7 to 12 carbon atoms, an aryl residue having from 6 to 12 carbon atoms, or the group having the formula:

$$-COZ_1$$

wherein $Z_1$ has the same significance as Z as hereinbefore defined or $Z_1$ is a group $-NR_5R_6$ wherein $R_5$ is hydrogen or an alkyl residue having from 1 to 4 carbon atoms and $R_6$ is hydrogen, an alkyl residue having from 1 to 20 carbon atoms, a cycloalkyl residue having from 5 to 12 carbon atoms, an aralkyl residue having from 7 to 12 carbon atoms or an aryl residue having from 6 to 12 carbon atoms.

When one or more of $R_1$, $R_2$, $R_3$ and $R_4$ is an alkyl residue, examples are methyl, ethyl, n-propyl, isopropyl, sec butyl, t-butyl, sec amyl, t-amyl (1,1-dimethylbutyl), capryl (2-octyl) and isononyl (ex mixed isomeric nonenes) residues. Preferably however the alkyl residue contains from 1 to 4 carbon atoms, the most preferred alkyl residue being methyl.

When one or more of $R_1$, $R_2$, $R_3$ and $R_4$ is a cycloalkyl residue, examples are cyclohexyl, 1-methyl cyclohexyl, cyclooctyl, cyclododecyl and adamantyl residues. Cycloalkyl residues having from 6 to 8 carbon atoms are preferred however and in particular the cyclohexyl and 1-methylcyclohexyl residues.

When one or more of $R_1$, $R_2$, $R_3$ and $R_4$ is a cycloalkyalkyl residue, it may be for instance a cyclohexyl-octyl or cyclohexyl-hexyl residue. Preferred however are cycloalkyl-alkyl residues having from 7 to 9 carbon atoms, especially cyclohexyl-methyl and 2-cyclohexyl-prop-2-yl residues.

Examples of combinations of substituents $R_1$, $R_2$, $R_3$ and $R_4$ are set out in the following table:

TABLE

| $R_1$ | $R_2$ | $R_3$ | $R_4$ |
|---|---|---|---|
| H | H | H | H |
| $CH_3$ | H | H | H |
| H | $CH_3$ | H | H |
| $CH_3$ | H | $CH_3$ | H |
| $CH_3$ | H | H | $CH_3$ |
| $CH_3$ | $CH_3$ | $CH_3$ | $CH_3$ |
| $C_2H_5$ | H | H | H |
| H | $C_2H_5$ | H | H |
| H | $C_2H_5$ | $CH_3$ | H |
| $C_2H_5$ | H | H | $C_2H_5$ |
| n-$C_3H_7$ | H | H | H |
| n-$C_3H_7$ | H | H | n-$C_3H_7$ |
| iso-$C_3H_7$ | H | H | H |
| H | iso-$C_3H_7$ | H | H |
| iso-$C_3H_7$ | H | H | iso-$C_3H_7$ |
| sec-$C_4H_9$ | H | H | H |
| sec-$C_4H_9$ | H | H | sec-$C_4H_9$ |
| t-$C_4H_9$ | H | H | H |
| H | t-$C_4H_9$ | H | H |
| t-$C_4H_9$ | H | $CH_3$ | H |
| t-$C_4H_9$ | H | H | $CH_3$ |
| t-$C_4H_9$ | H | H | t-$C_4H_9$ |
| sec-amyl | H | H | H |
| sec-amyl | H | H | sec-amyl |
| 1,1-dimethylpropyl | H | H | H |
| 1,1-dimethylpropyl | H | H | 1,1-dimethylpropyl |
| 1,1-dimethylbutyl | H | H | H |
| 1,1-dimethylbutyl | H | H | 1,1-dimethylbutyl |
| 2-octyl | H | H | H |
| cyclohexyl | H | H | H |
| 1-methylcyclohexyl | H | H | H |
| cyclohexylmethyl | H | H | H |
| 2-cyclohexylprop-2-yl | H | H | H |

Thus, although, in particular instances, each of the substituents $R_1$, $R_2$, $R_3$ and $R_4$ may be other than hydrogen, for instance, they may each be methyl, it is preferred in general, that at least two of these substituents are hydrogen. In particular, it is preferred that $R_2$ and / or $R_3$ are non-bulky substituents for instance a hydrogen atom, methyl or ethyl groups. However, if when one of the substituents $R_2$ and $R_3$ is a bulky group such as t-butyl group, then the other substituent is preferably hydrogen. Furthermore, it is to be understood that it is unlikely that bulky groups such as t-butyl groups will be situated on adjacent carbon atoms of the cyclohexyl residue.

Apart from 0° and hydrogen, Y may also be a methyl, ethyl, n-propyl, isopropyl, n-butyl, sec-butyl, benzyl, α-methylbenzyl, p-methylbenzyl or an α-naphthylbenzyl residue. However, particularly preferred substituents Y are H, O and straight- or branched alkyl groups having from 1 to 4 carbon atoms, the most preferred substituents Y being 0°, hydrogen and methyl residues.

Preferably, Z is hydrogen.

Examples of alkyl or substituted alkyl residues Z or $Z_1$ are methyl, ethyl, n-propyl, n-butyl, sec-butyl, t-butyl, n-hexyl, n-octyl, 2-ethylhexyl n-nonyl, n-decyl, n-undecyl, n-dedecyl, n-tridecyl, n-tetradecyl, n-hexadecyl, n-octadecyl, eicosyl, β-hydroxyethyl and β-cyanoethyl residues. Preferred alkyl or substituted alkyl residues Z or $Z_1$ are those having from 1 to 12 carbon atoms.

When Z or $Z_1$ is an alkenyl residue having from 2 to 20 carbon atoms, examples of such residues are vinyl, allyl, methylallyl, 3-hexenyl, 4-octenyl, 6-decenyl, 10-undecenyl and 8-octadecenyl residues, preferred alkenyl residues Z or $Z_1$ being allyl and methallyl residues.

Examples of alkynyl residues Z or $Z_1$ are propargyl, but-1- and 2-ynyl, pent-1-ynyl, hex-1-ynyl, oct-1-ynyl, dec-1-ycyl, dodec-1-ynyl, tetradec-1-ynyl and octadec-1-ynyl, preferred alkynyl residues Z or $Z_1$ being propargyl and methyl propargyl residues.

When Z or $Z_1$ is a cycloalkyl residue, it may be a cyclooctyl or cyclodecyl residue but is preferably a cyclopentyl or cyclohexyl residue.

Aralkyl residues Z or $Z_1$ may be, for instance, benzyl, α, α-dimethyl benzyl or α-methylbenzyl residues.

Aryl residues Z or $Z_1$ include phenyl, tolyl, naphthyl and p-t-butylphenyl residues.

When $Z_1$ is a group having the formula $NR_5R_6$, examples of such residues —$COZ_1$ are carbamoyl, N-methylcarbamoyl, N-ethyl-carbamoyl, N-n-propylcarbamoyl, N-isopropylcarbamoyl, N-n-butylcarbamoyl, N-n-pentylcarbamoyl, N-n-octyl-carbamoyl, N-n-decylcarbamoyl, N-n-dodecyl-carbamoyl, N-n-octadecylcarbamoyl, N-n-eicosylcarbamoyl, N-allylcarbamoyl, N-methylallylcarbamoyl, N-undecenylcarbamoyl, N-cyclopentylcarbamoyl, N-cyclohexylcarbamoyl, N-methylcyclohexylcarbamoyl, N-cyclododecylcarbamoyl, N-(1- and 2-perhydronaphthyl) carbamoyl, N-adamantylcarbamoyl, N-cyclopentylmethylcarbamoyl, N-benzylcarbamoyl, N-(β-phenethyl)carbamoyl, N-(1- and 2-naphthylmethyl)carbomoyl, N-phenylcarbamoyl N-(o-, m- and p-tolyl)carbamoyl, N-(2,4- and 2,6-xylyl) carbamoyl, N-(α- and β-naphthyl)carbamoyl, N,N-dimethylcarbamoyl, N-methyl-N-ethyl-carbamoyl, N,N-diethylcarbamoyl, N,N-diisopropyl-carbamoyl, N,N-di-n-propylcarbamoyl, N,N-di-n-butylcarbamoyl and N,N-diisobutyl-carbamoyl residues.

Examples of salts of the compounds of formula I are those formed from the amine function of the compounds of formula I with inorganic or organic acids, for instance hydrogen chloride, sulphuric acid, phosphoric acid, carbonic acid, acetic acid, maleic acid, malic acid, oxalic acid and tartaric acid.

Specific examples of compounds of formula I include:

Where Z = H: Y = H 4-(4'-Hydroxycyclohexyl)-2,2,6,6-tetramethylpiperidine 4-(4'-Hydroxy-3'-methyl-cyclohexyl)-2,2,6,6-tetramethyl-piperidine
4-(3', 5'-Dimethyl-4'-hydroxycyclohexyl)-2,2,6,6-tetramemthylpiperidine
4-(3', 5'-Diisopropyl-4'-hydroxycyclohexyl)-2,2,6,6-tetramethylpiperidine
4-(3't-Butyl-4'-hydroxycyclohexyl)-2,2,6,6-tetramethylpiperidine 4-(3', 5'-di-t-Butyl-4'-hydroxycyclohexyl)-2,2,6,6-tetramethylpiperidine
4-(3'-n-Hexyl-4'-hydroxycyclohexyl)-2,2,6,6-tetramethylpiperidine.
4[1'-Hydroxy-3'-(2''-octyl)-cyclohexy]-2,2,6,6-tetramethylpiperidine. 4-(3'-t-Butyl-4'-hydroxy-5'-methyl-cyclohexyl)-2,2,6,6-tetramethylpiperidine
4-(3'-Cyclohexyl-4'-hydroxycyclohexyl)-2,2,6,6-tetramethylpiperidine
4-(3'-cyclohexylmethyl-4'-hydroxycyclohexyl)-2,2,6,6-tetramethylpiperidine
4-(2'-Methyl-4'-hydroxycyclohexyl)-2,2,6,6-tetramethylpiperidine.

Where Z = H; Y = 0°

4-(4'-Hydroxycyclohexyl)-2,2,6,6-tetramethylpiperidine 4-(4'-Hydroxy-3'-methylcyclohexyl)-2,2,6,6-tetramethylpiperidine-1-oxyl
4-(3', 5'-hydroxycyclohexyl)-2,2,6,6-tetramethylpiperidine-1-oxyl
4-(3'-n-Hexyl-4'-hydroxycyclohexyl)-2,2,6,6-tetramethylpiperidiene-1-oxyl
4-(3'-Cyclohexyl-4'-hydroxycyclohexyl)-2,2,6,6-tetramethylpiperidine-1-oxyl Where Z = H; Y = Hydrocarbyl 4-(4'-Hydroxycyclohexyl)-1,2,2,6,6-pentamethylpiperidine
4-(4'-Hydroxy-3'-methylcyclohexyl)-1,2,2,6,6-pentamethylpiperidine 1-Benzyl-4-(3'-t-butyl-5'-methylcyclohexyl)-2,2,6,6-tetramethylpiperidine Where Z = Hydrocarbyl; Y = H 4-(4'-Methyoxycyclohexyl)-2,2,6,6-tetramethylpiperidine
4-(4'-n-Butyloxycyclohexyl)-2,2,6,6-tetramethylpiperidine
4-(4'-n-Butyloxy-3'-5'-diisopropylcyclohexnyl)-2,2,6,6-tetramethylpiperidine
4-(4'-Dodecyloxy-3'-methylcyclohexyl)-2,2,6,6-tetramethylpiperidine
4-(4'-Dodecyloxy-3'-methylcyclohexyl)-2,2,6,6-tetramethylpiperidine
4-(4'-Benzyloxy-3'-n-hexylcyclohexyl)-2,2,6,6-tetramethylpiperidine Where Z = Hydrocarbyl: Y = O°

4-(4'-Methoxycyclohexnyl)-2,2,6,6-tetramethylpiperidine-1-oxyl
4-(4'-Dodecyloxy-3'-methylcyclohexyl)-2,2,6,6-tramethylpiperidine-1-oxyl
4-(4'-Bensyloxy-3'-n-bexylcyclohexyl)-2,2,6,6-tetramethylpiperidine-1-oxyl Where Z = Hydrocarbyl: Y = Hydrocarbyl 4-(4'-Methoxycyclohexyl)-1,2,2,6,6-pentamethylpiperidine 4-(4'-n-Butyloxy-3', 5'-diisopropylcyclohexyl)-1-n-butyl-2,2,6,6-tetramethylpiperidine
4-(4'-Benzyloxy-3'-n-hexylcyclohexyl)-1-benzyl-2,2,6,6-tetramethylpiperidine
4-(4'-Butyloxycyclohexyl)-1,2,2,6,6-pentamethylpiperidine Where Z = —C—$Z_1$; Y= H
       ||
       O 4-(4'-Acetyloxycyclohexyl)-2,2,6,6-tetramethylpiperidine
4-(4'-n-Butylryloxycyclohexyl)-2,2,6,6-tetramethylpiperidine
4-(4'-n-Octanoylcoxycyclohexyl)-2,2,6,6-tetramethylpiperidine
4-(4'-n-Decanoyloxycyclohexyl)-2,2,6,6-tetramethylpiperidine
4-(4'-Stearcyloxycyclohexyl)-2,2,6,6-tetramethylpiperidine
4-(4'-Benzoyloxy -3', 5'-dimethylcyclohexyl)-2,2,6,6-tetramethylpiperidine
4-(4'-Acetyloxy-3'-cyclohexylcyclohexyl)-2,2,6,6-tetramethylpiperidine
4-(4'-n-Decanoyloxy-3'-n-hexylcyclohexyl)-2,2,6,6-tetramethylpiperidine 4-(4'- carbamoyloxycyclohexyl)2,2,6,6-tetramethyl-piperidine 4-(4'-N-Methylcarbamoyloxycyclohexyl)-2,2,6,6-tetramethylpiperidine 4-(4'-N-n-Hexylcarbomyloxy-3'-methylcyclohexyl)-2,2,6,6-tetramethylpiperidine 4-(4'-N-n-Dodecylcarbamoyloxy-3'-t-butyl-5-methylcyclohaxyl)-2,2,6,6-tetramethylpiperidine 4-(4'-N-p-Teluylcarbamoy-cyclohexyl)-2,2,6,6-tetramethylpiperidine 4-(3'-t-Butyl-4'-N-phenylcarbamoyloxy cyclohexyl)-2,2,6,6-tetramethylpiperidine Where $Z = -\underset{\underset{O}{\|}}{C}Z_1$; $Y = O^\circ$ 4-(4'-Acetylcxycyolohexyl)-2,2,6,6-tetramethyl-piperidine-1-oxyl 4-(4'-n-Octanoyloxycyclohexyl)-2,2,6,6-tetramethylpiperidine-1-oxyl 4-(4'-Stearoylcxycyclochexyl)2,2,6,6-tetramethyl-piperidine-1-oxyl 4-(4'-Benzoyloxy-3', 5'-dimethylcyclohexyl)-2,2,6,6-tetramethylpiperidine-1oxyl 4-(4'-n-Dctancyloxy-3'-n-hexylcyclohexyl)-2,2,6,6-tetramethylpiperidine-1-oxyl 4-(4'-N-Methylcarbamoyloxycyclohexyl)-2,2,6,6-tetramethyl-piperidine-1-oxyl 4(4'-N-n-Dodecylcarbamoyloxy-3'-t-butyl-5-methyl-cyclohexyl)-2,2,6,6-tetramethylpiperidine-1-oxyl 4-(4'-n-p-Tolycarbamoyloxy-cyclohexyl)-2,2,6,6-tetramethylpiperidine-1-oxyl Where $Z = -\underset{\underset{O}{\|}}{C}Z_1$; $Y = $ Hydrocarbyl 4-(4'-Acetyloxycyclohexyl)-1,2,2,6,6-pentamethyl-piperidine 4-(4'-n-Butyloxycyclohexyl)-1,2,2,6,6-pentamethyl-piperidine 1-Benzyl-4-(4'-benzoyloxy-3', 5'-dimethylcyclohex-yl)-2,2,6,6-tetramethylpiperidine 4-(4'-N-Methylcarbamcyclohexyl)-1,2,2,6,6-petamethylpiperidine 1-Benzyl-4-(4'-N-Dodecylcarbamoylcxy-3'-t-butyl-5-methylcyclohexyl)-2,2,6,6-tetramethylpiperidine 4-(4'-N-p-Tolycarbamoyloxy-cyclohexyl)-1,2,2,6,6-pentamethylpiperidine The present invention also provides a process of producing a compound of formula I wherein Y is other than O, Z is other than alkenyl, aryl, or aralkyl, comprising reducing a compound having the formula:

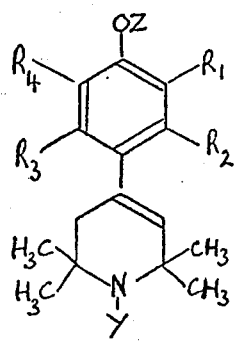

II or the formula:

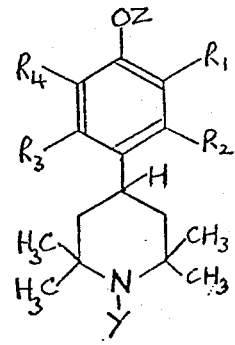

III wherein $R_1$, $R_2$, $R_3$, $R_4$, Z and Y have their previous significance and Y has its previous significance except that it cannot be O or aralkyl. The reduction may be effected using a hydrogenation technqiue.

The compounds of formula II wherein Z is hydrogen may be prepared by reacting the corresponding 2,2,6,6-tetramethylpiperidin-4-one or an inorganic or organic salt thereof with a phenolic compound of formula:

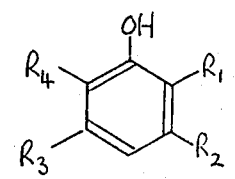

IV wherein $R_1$, $R_2$, $R_3$ and $R_4$ have their previous significance.

Advantageously, the reaction is effected in the presence of an acid catalyst such as sulphuric acid, p-toluene sulphonic acid or preferably hydrogen chloride, although other catalyst such as sulphur compounds, for instance mercaptans, may also be present, and in the presence of a solvent inert under the reaction conditions, for instance methanol, ethanol or 2-methoxyethanol.

The reaction is conveniently carried out at any temperature within the range of from 0°C and the reflux temperature of the reaction mixture, or a higher temperatures under pressure. The reactants may be employed in molar ratios of from 5:1 to 1:5, preferably from 3:1 to 1:3, and especially in molar ratios of about 1:1.

The compounds of formula II or III may be produced by reacting the compound of formula:

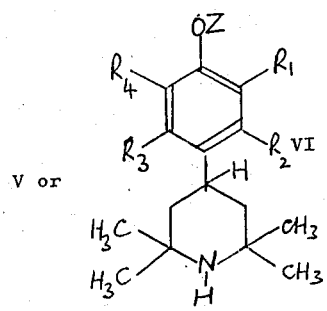

V or VI

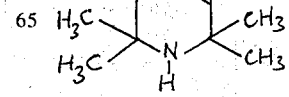

wherein Z, R₁, R₂, R₃ and R₄ have their previous significance, with an alkylating or alkenylating agent such as an alkyl or alkenyl halide.

When the group Z in the compounds of formula V or VI is a hydrogen atom, it may be necessary to protect the group —OZ during the reaction in order to prevent an undesirable simultaneous substitution on the oxygen and on the nitrogen atom.

N-substituted derivatives can also be obtained using a Leuckart-, Wallach- or Eschweiler-Clarke reaction, by reacting the compound of formula V or VI with formic acid and the appropriate aldehyde or ketone. In this way, the N-methtyl derivative may be obtained using formic acid and formaldehyde The compounds of formula II or III are conveniently isolated from the reaction mixture as their acid salts, and the free bases can then be obtained by reacting the salts with the stoichiometric amount of a base, such as sodium hydroxide or sodium carbonate, required to liberate the free base of formula II or III. If desired, the compound of formual II or III may then be further purified by conventional techniques.

The hydrogenation is conveniently effected in a solvent inert under the reaction conditions, for instance an aliphatic alcohol having from 1 to 4 carbon atoms, and in the presence of a hydrogenation catalyst for instance palladium, platinum, ruthenium, rhodium or Raney nickel. The catalyst may be used in pure form or supported upon an inert carrier such as alumina, calcium carbonate or carbon.

Alternatively, the hydrogenation may be carried out using as starting material a salt of a compound of formulae II or III. This can be a salt of the amine function with an inorganic acid such as hydrogen chloride or an organic acid such as acetic acid. When a salt of a compound of formulae II or III is used, the hydrogenation is preferably conducted in aqueous solution and to product of formula I is isolated by neutralisation of the aqueous solution with a base.

Subsequently if desired, the reduced product may be furher purified by conventional techniques such as crystallisation from a solvent.

Each of the hydrogenation procedures may be carried out under a wide variety of process conditions but preferably at elevated temperatures and pressures, for instance at a temperature within the range of from 50° to 200°C and at a pressure within the range of from 50 to 150 atmospheres of hydrogen.

Compounds of formula I in which Y is 0° may be conveniently produced by reacting compounds of formula I in which Y is H with an oxidising agent such as hydrogen peroxide or a per-acid such as per-formic acid. Preferably the oxidation is conducted in aqueous or alcoholic solution and in the presence of an oxidation catalyst such as tungstic acid or sodium tungstate.

In a less preferred embodiment, and N-substituted compound of formula I for instance a compound of formula I wherein Y is methyl, may be oxidised to give the corresponding compound of formula I in which Y is 0°.

When the substituent Y in the compound of formula I is other than 0° or H, these derivatives may be produced by reacting the corresponding compound of formula I in which Y is hydrogen with an alkylating, or aralkylating agent such as alkyl, or aralkyl halide respectively.

When Z is hydrogen in compound I then the group OH may require protection for instance by cylation, during the reaction to aovid undesirable simultaneous O- and N- substitution.

N-substituted compounds of formula I may also be prepared by a Leuckart, Wallach or Eschweiler-Clarke reaction, by reacting the compound of formula I wherein Y is H with formic acid and the appropriate aldehyde or ketone. In this way, for example, the N-methyl derivative may be obtained using formic acid and formaldehyde. Compounds of formula I in which Z is the group —COZ, where Z, is as hereinbefore defined may be conveniently prepared by reacting a compound of formula I in which Z is hydrogen with an esterification agent such as an acid, an acid chloride, and acid ester or an acid anhydride or an agent capable of forming a urethane grouping with the compound of formula I, such as an alkyl, alkenyl, aralkyl or aryl isocyanate.

The reaction is preferably conducted in a solvent inert under the reaction conditions such as benzene, toluene or xylene. Compounds of formula I in which Y is hereinbefore defined and Z is other than hydrogen or —COZ₁;

may be conveniently produced by reacting compounds of formula I in which Z is hydrogen with an alkali metal such as sodium or potassium followed by reaction with an alkylating, alkenylating, alkynylating or aralkylating agent such as an alkyl, alkenyl, alkynyl or aralkyl halide.

The reaction is preferably conducted in a solvent inert under the reaction conditions such as benzene, toluene or xylene. Salts of the compounds of formula I may be produced for example by the reaction of an acid with the corresponding compound of formula I, conveniently dissolved in an organic solvent. Salt formation is preferably conducted at ambient temperature although higher reaction temperature may be employed if desired.

The present invention still further provides a composition comprising an organic material and a stabilising amount of a compound having the formula I as hereinbefore defined.

Compounds of formula I, have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation, especially for low- and high-density polyethylene and polypropylene and polystyrene as well as polymers of butene-1, pentene-1, 3-methyl-butene-1, hexene-1, 4-methylpentene-1, 4-methylhexene-1 and 4,4-dimethyl-pentene-1, and also co- and ter-polymers of olefines, particularly of ethylene or propylene.

Other organic materials susceptible to degradiation by the effects of light and the properties of which are improved by the incorporation therein of a compound of formula I, include natural and synthetic polymeric materials, for instance natural and synthetic rubbers, the latter including, for example, homo-, co- and ter-polymers of acrylonitrile, butadiene and styrene.

Specific synthetic polymers include polyvinyl chloride, polyvinylidene chloride and vinyl chloride copolymers, polyvinyl acetate as well as condensation polymers derived from ether, ester (derived from carboxylic, sulphonic or carbonic acids) amide or urethane compounds; polyvinyl acetals, polyacrylates, such as polymers and copolymers of methyl acrylate, ethyl acrylate, methyl methacrylate and ethyl methacrylate; polyamides urea-formaldehyde and melamine-formaldehyde resins; cellulose plastics such as cellulose acetate, cellulose butyrate and cellulose nitrate. Certain of these polymers can, for instance, form the basis of surface coating media such as paints and lacquers having an oil or resin, for instance an alkyd or polyamide resin base.

The amount of the compound of formula I which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.1 to 5% by weight, more preferably within the range of from 0.1 to 2% by weight based on the weight of untreated organic material.

The compounds may be incorporated into the polymeric material by any of the known techniques for compounding additives with a polymer. For example, the compound and the polymer may be compounded in an internal mixer. Alternatively, the compound may be added as a solution or slurry in a suitable solvent or dispersant, for instance an inert organic solvent such as methanol, ethanol or acetone to powdered polymer and the whole mixed intimately in a mixer, and the solvent subsequently removed. As a further alternative the compound may be added to the polymer during the preparation of the latter, for instance at the latex stage of polymer production, to provide pre-stabilised polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers polyvinyl chloride stabilisers, nucleation agents, plasticizers, lubricants, emulsifiers, anti-static agents, flame-protectants, pigments, carbon black, asbestos, glass fibres, kaolin and talc.

The present invention therefore includes binary, tertiary and multi-component compositions containing the stabilisers of formula I together with one or more functional additives for polymers.

Examples of suitable antioxidants are those of the hindered phenol type such as those selected from the following groups: 1. Phenolic compounds having the general formula

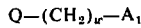

Q—(CH$_2$)$_w$—A$_1$ wherein
Q is

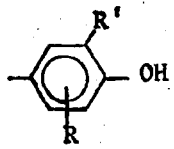

A$_1$ is —CR(COOR'')$_2$

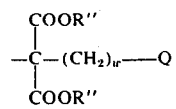

R is hydrogen or lower alkyl
R' is lower alkyl
R'' is alkyl group having from 6 – 24 carbon atoms
w is an integer from 0 to 4.

Illustrative examples of the compounds shown above are:
di-n-octadecyl-α-(3,5-di-t-butyl-4-hydroxy-benzyl) malonate
di-n-octadecyl-α-(3-t-butyl-4-hydroxy-5-methylbenzyl) malonate which is disclosed in the Netherlands Pat. No. 6,711,199, Feb. 19, 1968
di-n-octadecyl-α,α'bis-(3-t-butyl-4-hydroxy-5-methylbenzyl) malonate which is disclosed in the Netherlands Pat. No. 6,803,498, September 18, 1968.

2. Phenolic compounds having the general formula Q-R$_a$ Q is as above and R$_a$ is lower alkyl or hydrogen.

Illustrative examples of the compounds shown above are:
2,6-di-t-butyl-p-cresol
2-methyl-4,6-di-t-butylphenol and the like
2,6-di-Octadecyl-p-cresol 3. Phenolic compounds having the formula

Q—C$_w$H$_{2w}$—Q

Q and w are as above.
Illustrative examples of the compounds shown are:
2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(2-t-methylcyclohexyl)-4-methylphenol]
2,2'-methylene-bis(3-t-butyl-5-ethylphenol)
4,4'-methylene-bis(3,5-di-t-butylphenol)
4,4'-methylene-bis(3-t-butyl-5-methylphenol)
2,2'-methylene-bis(3-t-butyl-5-methylphenol) and the like.

4. Phenolic compounds having the formula:

R$_a$—O—Q

Q and R$_a$ are as above.
Illustrative examples of such compounds are:
2,5-di-t-butylhydroquinone
2,6-di-t-butylhydroquinone
2,5-di-t-butyl-4-hydroxyanisole 5. Phenolic compounds having the formula:

Q—S—Q.

Q is as above.
Illustrative examples of such compounds are:
4,4'-thiobis-(2-t-butyl-5-methylphenol)
4,4'-thiobis-(2-t-butyl-6-methylphenol)
2,2'-thiobis-(6-t-butyl-4-methylphenol)

4,4'-thiobis-(2-methyl-5-t-butylphenol)
6. Phenolic compounds having the formula

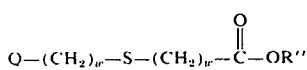

Q, w and RII are as above.
Illustrative examples of such compounds are:
octadecyl-(3,5-dimethyl-4-hydroxybenzylthio)-acetate
dodecyl-(3,5-di-t-butyl-4-hydroxybenzylthio)-propionate 7. Phenolic compounds having the formula

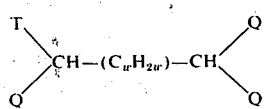

wherein T is hydrogen,
w and Q as defined above.
Illustrative examples of such compounds are:
1,1,3-tris(3,5-dimethyl-4-hydroxyphenyl)-propane
1,1,3-tris(5-t-butyl-4-hydroxy-2-methylphenyl)-butane
1,1,5,5-tetrakis-(3'-t-butyl-4'-hydroxy-6'-methylphenyl)-n-pentane 8. Phenolic compounds having the formula:

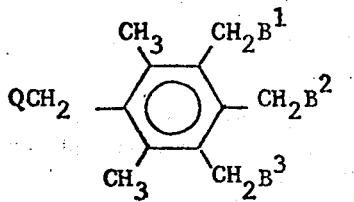

wherein $B^1$, $B^2$ and $B^3$ are hydrogen, methyl or Q, provided that when $B^1$ and $B^3$ are Q then $B^2$ is hydrogen or methyl and when $B^2$ is Q then $B^1$ and $B^3$ are hydrogen or methyl. Illustrative examples of such compounds are:
1,4-di(3,5-di-t-butyl-4-hydroxybenzyl)-2,3,5,6-tetramethylbenzene
1,3,5-tri(3,5-di-t-butyl-4-hydroxybenzyl)-2,4,6-trimethylbenzene 8. Phenolic compounds having the formula

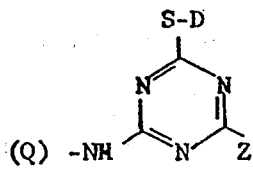

wherein Z is NHQ, —S—D— or —O—Q
D is alkyl group having from 6 – 12 carbon atoms or —($C_wH_{2w}$)—S—R''
Illustrative examples of such compounds are:
2,4-bis-(n-octylthio)-6-(3,5-di-t-butyl-4-hydroxyanilino)-1,3,5-triazine
6-(4-hydroxy-3-methyl-5-t-butylanilino)-2,4-bis-(n-octyl-thio)-1,3,5-triazine
6-(4-hydroxy-3,5-dimethylanilino)-2,4-bis-(n-octyl-thio)-1,3,5-triazine
6-(4-hydroxy-3,5-di-t-butylanilino)-2,4-bis-(n-octyl-thio)-1,3,5-triazine
6-(4-hydroxy-3,5-di-t-butylanilino)-4-(4-hydroxy-3,5-di-t-butylphenoxy)-2-(n-octylthio)1,3,5-triazine
2,4-bis(4-hydroxy-3,5-di-t-butylanilino)-6-(n-octyl-thio)-1,3,5-triazine The above phenolic triazine stabilizers are more fully described in U.S. Pat. No. 3,255,191.

10. Phenolic compounds having the formula:

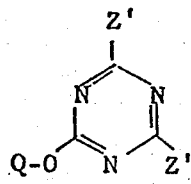

wherein Z' is —O—Q, —S—D or —S—($C_wH_{2w}$)—SD.
Q, w and D are as above. Illustrative examples of such compounds are:
2,3-bis-(3,5-di-t-butyl-4-hydroxyphenoxy)-6-(n-octylthio)-1,3,5-triazine
2,4,6-tris-(4-hydroxy-3,5di-t-butylphenoxy)-1,3,5-triazine
6-(4-hydroxy-3,5-di-t-butylphenoxy)-2,4-bis-(n-octylthioethylthio)-1,3,5-triazine
6-(4-hydroxy-3-methylphenoxy)-2,4-bis(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthiopropylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine. The above phenolic triazine stabilizers are more fully described in U.S. Pat. No. 3,255,191.

11. Phenolic compounds having the formula

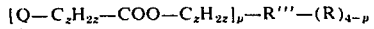

wherein p is an integer from 2 to 4 and R''' is a tetravalent radical selected from aliphatic hydrocarbons having from 1 to 30 carbon atoms, aliphatic mono- and di-thioethers having from 1 to 30 carbon atoms, aliphatic mono- and diethers having from 1 to 30 carbon atoms and z is an integer from 0 to 6. Illustrative examples of such compounds are

SUB-CLASS I n-Octadecyl-3-(3,5-di-t-butyl-4-hydroxyphenyl)-propionate
n-Octadecyl-2-(3,5-di-t-butyl-4-hydroxyphenyl)-acetate
n-Octadecyl-3,5-di-t-butyl-4-hydroxybenzoate
n-Hexyl-3,5-di-t-butyl-4-hydroxyphenylbenzoate
n-Dodecyl-3,5-di-t-butyl-4-hydroxyphenylbenzoate
Neo-dodecyl-3-(3,5-di-t-butyl-4-hydroxyphenyl)-propionate
Dodecyl-β-(3,5-di-t-butyl-4-hydroxyphenyl)-propionate
Ethyl-α-(4-hydroxy-3,5-di-t-butylphenyl)-isobutyrate
Octadecyl-α-(4-hydroxy-3,5-di-t-butylphenyl)-isobutyrate
Octadecyl-α-(4-hydroxy-3,5-di-t-butylphenyl)-propionate

SUB-CLASS II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-Thiodiethanol bis(3,5-di-t-butyl-4-hydroxyphenyl) acetate
Diethyl glycol bis-[3,5-di-t-butyl-4-hydroxyphenyl) propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate 2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate

SUB-CLASS III 1,2-propylene glycol bis-[3-(3,5-di-t-butyl-4-hydroxyphenyl)propionate]
Ethylene glycol bis-[3-(3,5-di-t-butyl-4-hydroxyphenyl) propionate]
Neopentylglycol bis-[3-(3,5-di-t-butyl-4-hydroxyphenyl) propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl) propionate]
1,2,3-butanetriol tris-[3-(3,5-di-t-butyl-4-hydroxyphenyl)propionate]
2-hydroxyethyl 7-(3-methyl-5-t-butyl-4-hydroxyphenyl) heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl) propionate]

The above phenolic ester stabilizers of sub-classes I, II and III are more fully described in U.S. Pat. No. 3,330,859, Ser. No. 354,464, filed Mar. 24, 1964 and Ser. No. 359,460, filed Apr. 13, 1964, respectively 12. Phenolic compounds having the formula

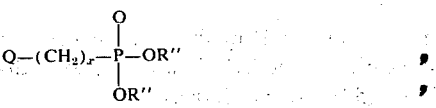

where x is an integer of 1 or 2. Illustrative examples of such compounds are
Di-n-octadecyl 3,5-di-t-butyl-4-hydroxybenzyl-phosphonate
Di-n-octadecyl 3-t-butyl-4-hydroxy-5-methylbenzyl-phosphonate
Di-n-octadecyl 1-(3,5-di-t-butyl-4-hydroxyphenyl)-ethanephosphonate
Di-n-tetradecyl 3,5-di-t-butyl-4-hydroxybenzyl-phosphonate
Di-n-hexadecyl 3,5-di-t-butyl-4-hydroxybenzyl-phosphonate
Di-n-decosyl-3,5-di-t-butyl-4-hydroxybenzyl-phosphonate
Di-n-octadecyl 3,5-di-t-butyl-4-hydroxybenzyl-phosphonate. The above di-(higher)alkyl phenolic phosphonates are more fully described in U.S. Pat. No. 3,281,505.

13. Phenolic compounds having the formula

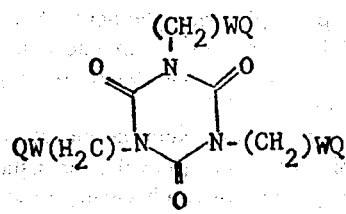

wherein W and Q are defined above. Illustrative examples of such compounds are:
tris-(3,5-di-t-butyl-4-hydroxybenzyl)isocyanurate
tris-(3-t-butyl-4-hydroxy-5-methylbenzyl)isocyanurate The above hydroxyphenylalkenyl isocyanurates are more fully described in U.S. Pat. No. 3,531,483. The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:

phenyl-1-naphthylamine
phenyl-2-naphthylamine
N,N'-diphenyl-p-phenylenediamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and polymerised 2,2,4-trimethyl-1,2-dihydroquinoline. Ultraviolet absorbers and light protectants include a. 2-2'-hydroxyphenyl)benzotriazoles, for instance 5'-methyl; 3',5'-di-t-butyl; 5'-t-butyl; 5-chloro-3', 5'-di-t-butyl; 5-chloro-3'-t-butyl-5'-methyl; 3'-sec. butyl-5'-tert.butyl; 3'-[α-methylbenzyl]-5'-methyl-;
3'-[α-methylbenzyl)-5'-methyl-5-chloro-; 4'-octoxy-; 3',5'-di-t-amyl; 3'-methyl-5'-carbamethoxyethyl]; 5-chloro-3',5'-di-t-amyl derivatives.

b. 2,4-bis-(2'-hydroxyphenyl)-6-alkyl-S-triazines, for instance the 6-ethyl or 6-undecyl derivatives.

c. 2-hydroxybenzophenones, for instance the 4-hydroxy,
4-methoxy, 4-octoxy-, 4-decyloxy-, 4-dodecyloxy-, 4,2',
4'-trihydroxy or 2'-hydroxy-4,4'-dimethoxy derivatives.

d. 1,3-Bis(2'-hydroxybenzoyl)-benzenes for instance,
1,3-bis-(2'-hydroxy-4'-hexyloxybenzoyl)benzene
1,3-bis-(2'-hydroxy-4'-octoxybenzoyl)benzene
1,3-bis-(2'-hydroxy-4'-dodecyloxybenzoyl)benzene e. Aryl esters from optionally substituted benzoic acids such as phenylsalicylate, octylphenylsalicylate, dibenzoyl resorcinol, bis-(4-tert.butylbenzoyl) resorcinol, benzoylresorcinol and 3,5-di-tert.butyl-4-hydroxybenzoic acid-2,4-di-tert.butyl phenyl ester and -octadecyl ester and -2-methyl-4,6-di-tert.butyl phenyl ester.

f. Acrylates, for instance
α-Cyano-β,β-diphenylacrylic acid ethyl- or iso-octyl ester, α-carbomethoxy-cinnamic acid, methyl- or butyl ester and N-(β-carbomethoxyvinyl)-2-methyl indoline.

g. Nickel compounds such as nickel complexes of 2,2'-thio-bis-(4-tert.octylphenol), for instance the 1:1 and 1:2 complexes, optionally having other liquids such as n-butylamine, triethanolamine or N-cyclohexyl-diethanolamine; nickel complexes of bis-(4-tert.octylphenyl) sulphone such as the 2:1 complex, optionally having other ligands such as 2-ethylcaproic acid; nickel dibutyl dithiocarbamates; nickel salts of 4-hydroxy-3,5-di-tert. butylbenzyl-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and h. Oxalic acid diamides, for instance
4,4'-dioctyloxyoxanilide
2,2'-dioctyloxy-5,5'-di-tert.butyl-oxanilide
2,2'-di-dodecyloxy-5,5'-di-tert.butyl oxanilide
2-ethoxy-5-tertiarybutyl-2'-ethyl-oxanilide
2-ethoxy-2'-ethyl-oxanilide mixtures of o- and p-methoxy and ethoxy-di-substituted oxanilides and the compound of formula:

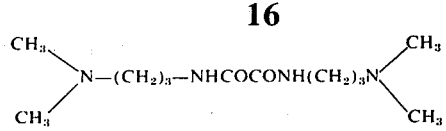

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-ditert.butylphenyl)phosphite.

Peroxide-decomposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I any further additive is advantageously employed in a proportion within the range of from 0.01 to 5% by weight, based on the weight of untreated polymeric material.

In binary combinations with one or more antioxidants listed above or in tertiary combinations with such antioxidants and U.V. absorbers listed above, the compounds of formula I provide very effective stabiliser packages in polyolefine formulations.

Some Examples will now be given. Parts and percentages are by weight unless otherwise stated.

EXAMPLE 1

4-(4'-Hydroxycyclohexyl)-2,2,6,6-tetramethylpiperidine 10 parts of 4-(4'-hydroxyphenyl)-2,2,6,6-tetramethylpiperidine were dissolved in 150 parts of ethanol and treated with 30 parts of water, the mixture being warmed to maintain solution. The solution was then hydrogenated using 3 parts of ruthenium on carbon (5%) catalyst at 125°C and 100 atmospheres of hydrogen. The catalyst was separated and the solvent evaporated under reduced pressure. The residue was dissolved in chloroform, dried with magnesium sulphate and evaporated under reduced pressure. The residue was crystallised from petroleum (b.p. 80°–100°C) to yield the desired product melting at 145°–150°C and having the following elemental analysis.

$C_{15}H_{29}NO$ required C, 75.26; H, 12.21; N, 5.85. found C, 75.27; H, 12.07; N, 5.78%.

The compounds of formula I listed in the following Table have been prepared from compounds of formula II or III using the method employed in Example 1.

TABLE 1

| Example Number | Product of formula I where Z=Y=H | | | | M.p °C | Molecular Formula | Analysis | | | | | |
|---|---|---|---|---|---|---|---|---|---|---|---|---|
| | $R_1$ | $R_2$ | $R_3$ | $R_4$ | | | Required (%) | | | Found (%) | | |
| | | | | | | | C | H | N | C | H | N |
| 2 | $CH_3$ | H | H | H | 123–7° | $C_{16}H_{31}NO$ | 75.83 | 12.33 | 5.53 | 75.99 | 12.27 | 5.36 |
| 3 | $CH_3$ | H | H | $CH_3$ | 163–5° | $C_{17}H_{33}NO$ | 76.34 | 12.44 | 5.24 | 76.17 | 12.55 | 5.02 |
| 4 | cyclo-hexyl | H | H | H | 44–7° | $C_{21}H_{39}NO$ | 78.44 | 12.23 | 4.36 | 78.32 | 12.17 | 4.13 |
| 5 | cyclo hexyl methyl | H | H | H | 145–7° | $C_{22}H_{41}NO$ | 78.74 | 12.32 | 4.17 | 78.94 | 12.32 | 3.95 |

EXAMPLE 6

4-(3′,5′-Dimethyl-4′-hydroxycyclohexyl)-1,2,2,6,6-pentamethylpiperidine

This compound was prepared from 4-(3′,5′-dimethyl-4′-hydroxyphenyl) 1,2,2,6,6-penta-methylpiperidine using the method employed in Example 1. The product melted at 119°–124°C and had the following elemental analysis:

$C_{18}H_{35}NO$ required C, 76.81; H, 12.53; N, 4.98. found C, 76.61; H, 12.33; N, 5.37%.

EXAMPLE 7

4-(4′-Acetyloxycyclohexyl)-2,2,6,6-tetramethylpiperidine 7 parts of 4-(4′-hydroxycyclohexyl)-2,2,6,6-tetramethylpiperidine were dissolved in xylene by warming 1.7 parts of acetic acid and 0.5 part of tetra-n-butyl-ortho-titanate were added and the solution allowed to stir and reflux for 48 hours. Water was continuously removed from the reaction. The xylene was removed under reduced pressure and the residue treated with 0.5 part carbon, 0.5 part sodium carbonate and water. The mixture was stirred and heated at reflux for 1 hour. The mixture was then filtered and the filtrate extracted with ether. The organic layer was dried over magnesium sulphate and evaporated under reduced pressure. The residue was distilled under reduced pressure to yield the desired product boiling at 114°–7°C/0.1mm and having the following elemental analysis:

$C_{17}H_{31}NO_2$ requires C, 72.55; H, 11.10; N, 4.98. found C, 72.30; H, 11.35; N, 4.84%.

The compounds of formula I where $R_1$, $R_2$, $R_3$, $R_4$ and Y are each hydrogen in Table 2 have been prepared using the method employed in Example 7.

EXAMPLE 12

4-(4′-N-Methylcarbamoyloxycyclohexyl)-2,2,6,6-tetramethylpiperidine

3 Parts of 4-(4′-hydroxycyclohexyl)-2,2,6,6-tetramethylpiperidine were dissolved in dry benzene and 0.81 part of methyl isocyanate was added. A crystal of 1,1-diazabicyclo[2,2,2]octane was added and the solution heated at reflux for 15 hours. The benzene was removed under reduced pressure and the residue triturated with petroleum ether (b.p. 60°–80°C). The solid was crystallised from petroleum (b.p. 60°–80°C) to yield the desired product melting at 155°–158°C and having the following elemental analysis.

$C_{17}H_{32}N_2O_2$ requires C, 68.88; H, 10.88; N, 9.45. found C, 69.01; H, 10.69; N, 9.35%.

EXAMPLE 13

4-(4′-N-p-Tolylcarbamoyloxy-cyclohexyl)2,2,6,6-tetramethylpiperidine

This compound was prepared from 4-(4′-hydroxycyclohexyl)-2,2,6,6-tetramethylpiperidine and p-toluene isocyanate in a manner similar to that described in Example 12. The solid reaction product was crystallised from petroleum ether (b.p. 80°–100°C) to yield the desired product melting at 139°–141°C and having the following elemental analysis:

$C_{23}H_{36}N_2O_2$ requires C, 74.15; H, 9.45; N, 7.52. found C, 74.26; H, 9.59; N, 7.24%.

EXAMPLE 14 AND 15

Application in polypropylene 38 parts of polypropylene were homogenised with 0.076 part of n-octadecyl-β-(4′-hydroxy-3′5′-t-butylphenyl) propionate in a kneading machine over a period of 3 minutes. 0.19 part of the product of Example 1 or 10 was then added and homogenisation was continued for a further 7 minutes.

The homogenised mixture was removed from the kneader and pressed to a thickness of 2–3 mm in a press at a temperature of 200°C. This composition was compression moulded at 260°C for 6 mins. into film of 0.1 mm thickness. The resulting film was quenched in cold water.

A section measuring 44 × 100 mm was separated from the 0.1 mm annealed polypropylene foil and expressed to light irradiation in a fademeter device consisting of a circular bank of 28 alternate sunlight and

TABLE 2

| Example Number | Z | B.p °C. | Molecular Formula | Analysis | | | | | |
|---|---|---|---|---|---|---|---|---|---|
| | | | | Required (%) | | | Found (%) | | |
| | | | | C | H | N | C | H | N |
| 8 | $n\text{-}C_3H_7CO$ | 150°/0.5mm | $C_{19}H_{35}NO_2$ | 73.74 | 11.40 | 4.53 | 73.95 | 11.63 | 4.37 |
| 9 | $n\text{-}C_7H_{15}CO$ | 160–3°/0.1mm | $C_{23}H_{43}NO_2$ | 75.56 | 11.86 | 3.83 | 75.82 | 11.95 | 3.78 |
| 10 | $n\text{-}C_9H_{19}CO$ | 189–90°/0.2mm | $C_{23}H_{47}NO_2$ | 76.28 | 12.03 | 3.56 | 76.12 | 11.96 | 3.36 |
| 11 | $n\text{-}C_{17}H_{33}CO$ | 235–6°/0.2mm | $C_{33}H_{63}NO_2$ | 78.35 | 12.55 | 2.77 | 78.61 | 12.43 | 2.52 | blacklight lamps. The sunlight lamps were 2 feet long, 20-watt fluorescent lamps characterised by a peak emission of 3100 Angstom units; the blacklight lamps were 2 feet long, 20-watt ultraviolet lamps characterised by a peak emission of 3500 Angstrom units. The sample was rotated concentrically within the bank of lamps so that the radiation therefrom was uniformly distributed over the section under test.

The exposed sample was examined periodically and the time at which the sample reached 50% of the initial elongation at break was noted.

The time for the elongation of a control sample (not containing the product of Example 1 or 10) to decrease to 50% of the initial elongation was then determined.

The results obtained are summarised in the following Table 3.

TABLE 3

| Example | Additive | Time to 50% initial elongation at break (hours) |
|---|---|---|
| — | None | 185 |
| 14 | 4-(4'-hydroxycyclohexyl)-2,2,6,6-tetramethylpiperidine (product of Example 1) | 725 |
| 15 | 4-(4'-decanoyloxycyclohexyl)-2,2,6,6 tetramethylpiperidine (product of Example 10) | 710 |

The results in the Table demonstrate clearly the improved light stability of the polypropylene foil containing a stabiliser according to this invention compared with a control polypropylene foil.

EXAMPLE 16

4-(40'-Hydroxycyclohexyl)-1,2,2,6,6-pentamethyl-piperidine 9 parts of 4(4'-hydroxycyclohexyl)-2,2,6,6-tetramethylpiperidine were dissolved in 12 parts of formic acid and the solution treated with 4 parts of 37% formaldehyde solution. The mixture was heated under a reflux condenser on a steam bath overnight then poured into water and the solution rendered alkaline by the addition of excess sodium carbonate solution. The alkaline solution was extracted with ether, dried over magnesium sulphate and the solvent evaporated. The residue was dissolved in 70 parts of 10% sulphuric acid and heated at reflux for 2 hours. The acid solution was poured into water and rendered alkaline by the addition of solid sodium carbonate. The alkaline solution was extracted with ether, dried over magnesium sulphate and the solvent evaporated. The residue was crystallised from petroleum ether (b.p. 60°–80°C.) to yield the desired product melting at 107°–9°C. and having the following elemental analysis:

$C_{16}H_{31}NO$ requires C, 75.83; H, 12.33; N, 5.53. found C, 76.08; H, 12.19; N, 5.63%.

EXAMPLE 17

4-(4'-Hydroxycyclohexyl)-2,2,6,6-tetramethylpiperidine-1-oxyl 4.0 parts by weight of 4-(4'-hydroxycyclohexyl)-2,2,6,6-tetramethylpiperidine and 0.3 part by weight of benzyl trimethylammonium chloride were dissolved in 50 parts by weight of methanol. 0.3 part by weight of sodium tungstate, dissolved in 3 parts by weight of water were added to the methanolic solution. 6.0 parts by weight of water were then added, care being taken to maintain solution. 5.0 parts by weight of 30% hydrogen peroxide, dissolved in methanol were added dropwise with stirring to the amine solution. When the addition was complete the solution was stirred at room temperature for 2 hours, and then allowed to stand in the absence of light overnight. The solution was then evaporated to dryness under reduced pressure, the residue dissolved in ether and washed with 10% sulphuric acid and water. After drying over magnesium sulphate the ethereal layer was evaporated and the residue distilled under reduced pressure to give the desired product boiling at 104°C/0.1 mm and having the following elemental analysis:

$C_{15}H_{28}NO_2$ requires C, 70.82; H, 11.09; N, 5.50. found C, 70.94; H, 10.89; N, 5.30%.

EXAMPLE 18

4-(4'-n-Butyloxycyclohexyl)-2,2,6,6-tetramethyl piperidine 8.2 parts of 4-(4'-n-Butyloxyphenyl)-2,2,6,6-tetramethylpiperidine were hydrogenated using the method employed in Example 1. The residue obtained after evaporation of the solvent was distilled under reduced pressure to yield the product boiling at 128°–130°C/0.5 mm and having the following elemental analysis:

$C_{19}H_{37}NO$ requires C, 77.23; H, 12.62; N, 4.74. found C, 77.17; H, 12.43; N, 5.22%.

EXAMPLE 19

4-(4'-Dodecyloxycyclohexyl)-2,2,6,6-tetramethyl-piperidine 9.0 parts of 4-(4'-dodecyloxyphenyl)-2,2,6,6-tetramethylpiperidine were hydrogenated using the method employed in Example 1. The residue obtained after evaporation of the solvent was distilled under reduced pressure to yield the product boiling at 175°–178°C/0.1 mm and having the following elemental analysis:

$C_{27}H_{53}NO$ requires C, 79.54; H, 13.10; N, 3.44. found C, 79.28; H, 12.90; N, 3.63%.

EXAMPLE 20

4-[4'-N-(4''-Methylcyclohexyl)carbamoyloxycyclohexyl] 2,2,6,6-tetramethylpiperidine 8.5 parts of 4-[4'-N-p-tolylcarbamoyloxycyclohexyl] 2,2,6,6-tetramethylpiperidine were hydrogenated using the method employed in Example 1. The residue obtained after evaporation of the solvent was crystallised from a methanol - water mixture to yield the desired product melting at 105°–9°C and having the following elemental analysis:

$C_{23}H_{42}N_2O_2$ requires C, 72.97; H, 11.18; N, 7.40. found C, 73.08; H, 10.85; N, 7.34%.

EXAMPLE 21

4-[4'-N-n-Octadecylcarbamoyloxycyclohexyl]-2,2,6,6-tetramethylpiperidine 10.0 parts of 4(4'-N-n-octadecylcarbamoyloxyphenyl)-2,2,6,6-tetramethylpiperidine were hydrogenated using the method employed in Example 1. The residue obtained after evaporation of the solvent was treated with petroleum ether (b.p. 60°–80°C.) and the solid filtered. The filtrate was evaporated and distilled under reduced pressure to yield the product boiling at 130°C/0.01 mm and having the following elemental analysis:

$C_{34}H_{66}N_2O_2$ requires C, 76.34; H, 12.44; N, 5.24. found C, 76.35; H, 12.81; N, 4.70%.

EXAMPLE 22

Application in white-pigmented polyurethane films

A solution of Estane 5707 Fl (B.F. Goodrich; 25 parts) in dimethylformamide (75 parts) was treated with the following additives expressed as percentages of the polymers used: Bayertitan RFKD (5%), Santocel (3%), and product from Example 1 (1%). The solution was thoroughly mixed and drawn out on glass plates to a film of 400–500 μ thickness which was dried for 4 minutes at 50°C and then 6 minutes at 140°C. The final thickness of the dried film was 80–100 μ. The film samples were removed from the glass, mounted on white card and exposed in a Xenotest 450. One half of each of the samples was covered during exposure to enable a visual judgement of yellowing to be made. An unstabilised control sample was included during the exposure test. The samples were rated periodically in intervals of 100 hours.

| Formulation | Exposure time to distinct yellowing. Hours. |
|---|---|
| Control | <100 |
| 4-(4'-Hydroxycyclohexyl)-2,2,6,6-tetramethyl-piperidine (product of Example 1) | 400 |

EXAMPLE 23

Application in clear polyurethane films

A solution of of Estane 5707 Fl (B.F. Goodrich; 25 parts) in a 1:1 volume mixture of dimethylformamide and acetone (75 parts) was treated with the product from Example 1 (1% based on polymer). The solution was thoroughly mixed and drawn out on a glass plate to a film of 400–500 μ thickness. The film was dried and exposed in a manner similar to that employed in Example 22.

| Formulation | Exposure time to distinct yellowing Hours |
|---|---|
| Control | 150 |
| 4-(4'-Hydroxycyclohexyl) 2,2,6,6-tetramethylpiperidine (product of Example 1) | 500 |

EXAMPLE 24

Application of Crystal Polystyrene

100 Parts of crystal polystyrene pellets were dry blended with 0.25 part of the product from Example 1 and the dry blend was homogenised by extension. The stabilised pellets so obtained were injection moulded to form plaques 2 mm. thick. These plaques were exposed for 3000 hours in a "Xenotest 150" exposure unit, and any yelowing of the plaques was measured by determining the yellowness factor by means of the following equations:

$$\text{yellowness factor} = \frac{\Delta T_{(420)} - \Delta T_{(680)}}{T_{(560)}} \times 100$$

ps wherein the Δ T values represent the transmission loss of the sample at wavelengths of 420 mμ. and 680 mμ. respectively, after exposure in the Xenotest unit, and $T_{(560)}$ represents the transmission value of an unexposed sample at a wavelength of 560 mμ.

The yellowing factors were determined for the test sample and a control sample at 2000, 2500, and 3000 hrs.

| Formulation | Yellowing factor after | | |
|---|---|---|---|
| | 2000 Hr. | 2500 Hr. | 3000 Hr. |
| Control | 20.2 | 32.5 | 37.0 |
| 4-(4'-Hydroxycyclohexyl) 2,2,6,6-tetramethylpiperidine (product of Example 1) | 7.9 | 17.0 | 19.3 |

The results in Examples 14, 15, 22, 23 and 24 demonstrate the ability of the compounds of the invention to confer improved light stability to polyolefines, polystyrene and polyurethanes.

We claim:

1. A compound having the formula:

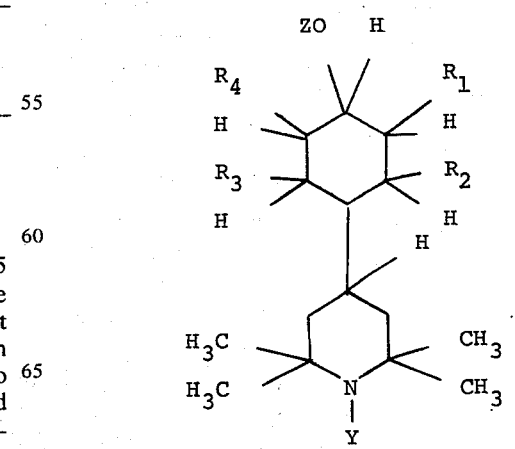

wherein $R_1$, $R_2$, $R_3$ and $R_4$ are the same or different and each is hydrogen, an alkyl having from 1 to 9 carbon atoms, a cycloalkyl having from 5 to 14 carbon atoms or a cycloalkyl-alkyl having from 7 to 14 carbon atoms, Y is hydrogen, O, an alkyl having from 1 to 4 carbon atoms, or an aralkyl having from 7 to 12 carbon atoms and being selected from the group selected of benzyl, α-methylbenzyl, p-methylbenzyl and α-naphthylbenzyl, and Z is hydrogen, an unsubstituted alkyl or alkyl substituted by hydroxy or cyano groups, said alkyl groups having from 1 to 20 carbon atoms, an alkenyl or alkynyl having from 2 to 20 carbon atoms, a cycloalkyl having from 5 to 12 carbon atoms, an aralkyl having from 7 to 12 carbon atoms and being selected from benzyl, α, α-dimethylbenzyl and α-methylbenzyl, an aryl having from 6 to 12 carbon atoms and being selected from phenyl, tolyl, naphthyl and p-t-butylphenyl, or the group having the formula:

$$-COZ_1$$

wherein $Z_1$ has the same significance as Z as hereinbefore defined, or $Z_1$ is a group $-NR_5R_6$ wherein $R_5$ is hydrogen or an alkyl having 1 to 4 carbon atoms and $R_6$ is hydrogen, an alkyl group having from 1 to 20 carbon atoms, a cycloalkyl group having from 5 to 12 carbon atoms, an aralkyl having from 7 to 12 carbon atoms as defined above or an aryl having from 6 to 12 carbon atoms as defined above, or hydrogen chloride, sulfuric acid, phosphoric acid, carbonic acid, acetic acid, maleic acid, malic acid, oxalic acid or tartaric acid salt of a compound of Formula I.

2. A compound as claimed in claim 1 wherein at least two of substituents $R_1$, $R_2$, $R_3$ and $R_4$ are hydrogen.

3. A compound as claimed in claim 2 wherein $R_2$ and/or $R_3$ are hydrogen, methyl or ethyl.

4. A compound as claimed in claim 3 wherein Y is O, hydrogen or a methyl.

5. A compound as claimed in claim 4 wherein Z is hydrogen.

6. A compound as claimed in claim 5 wherein the compound of formula I is a salt formed from the amine function of the compound of formula I with hydrogen chloride, sulphuric acid, phosphonic acid, carbonic acid, acetic acid, maleic acid, malic acid, oxalic acid or tartaric acid.

7. 4-(4'-hydroxycyclohexyl)-2,2,6,6-tetramethyl-piperidine.

8. 4-(4'-hydroxy-3'-methylcyclohexyl)-2,2,6,6-tetramethyl piperidine.

9. 4-(3',5'-dimethyl-4'-hydroxycyclohexyl)-2,2,6,6-tetramethyl-piperidine.

10. 4-(4'-hydroxycyclohexyl)-1,2,2,6,6-pentamethyl-piperidine.

* * * * *